United States Patent [19]
Abiuso et al.

[11] Patent Number: 5,213,576
[45] Date of Patent: May 25, 1993

[54] THERAPEUTIC POROUS BALLOON CATHETER

[75] Inventors: Christopher L. Abiuso; James E. Leone, both of Miami, Fla.

[73] Assignee: Cordis Corporation, Miami Lakes, Fla.

[21] Appl. No.: 714,003

[22] Filed: Jun. 11, 1991

[51] Int. Cl.⁵ .................................. A61M 29/00
[52] U.S. Cl. ........................... 604/96; 606/192; 604/102
[58] Field of Search .......... 604/52, 53, 93, 96, 604/101-103, 264, 280, 265; 606/192, 191, 193, 194; 128/207.15

[56] References Cited

U.S. PATENT DOCUMENTS

| | | |
|---|---|---|
| 797,676 | 8/1905 | Flowers .................. 604/96 |
| 3,173,418 | 3/1965 | Baran . |
| 3,981,299 | 9/1976 | Murray . |
| 4,417,576 | 11/1983 | Baran . |
| 4,423,725 | 1/1984 | Baran et al. . |
| 4,821,722 | 4/1989 | Miller et al. . |
| 4,994,033 | 2/1991 | Shockey et al. . |
| 5,041,090 | 8/1991 | Scheglov et al. .......... 604/101 |
| 5,049,132 | 9/1991 | Shaffer et al. . |
| 5,071,406 | 12/1991 | Jang ...................... 604/96 |
| 5,087,244 | 2/1992 | Wolinsky et al. . |
| 5,098,381 | 3/1992 | Schneider . |

FOREIGN PATENT DOCUMENTS

| | | |
|---|---|---|
| 0383429 | 8/1990 | European Pat. Off. . |
| WO89/12478 | 12/1989 | PCT Int'l Appl. . |
| 1069826 | 1/1984 | U.S.S.R. .............. 128/207.15 |

Primary Examiner—John D. Yasko
Assistant Examiner—Adam J. Cermak
Attorney, Agent, or Firm—Gerstman & Ellis

[57] ABSTRACT

A balloon catheter comprises a catheter shaft, and first and second balloons carried on the catheter shaft with the second balloon positioned to at least partly overlie and sealingly enclose the first balloon. A lumen is defined by the catheter shaft to communicate between a space located within the first balloon and a proximal end portion of the catheter shaft. The first and second balloons each define holes of a size to permit medication delivered through the lumen to pass outwardly through the perforations of both the first and second balloons. By such an arrangement, medication may be directly delivered over a wide area to tissue without tissue damage.

28 Claims, 2 Drawing Sheets

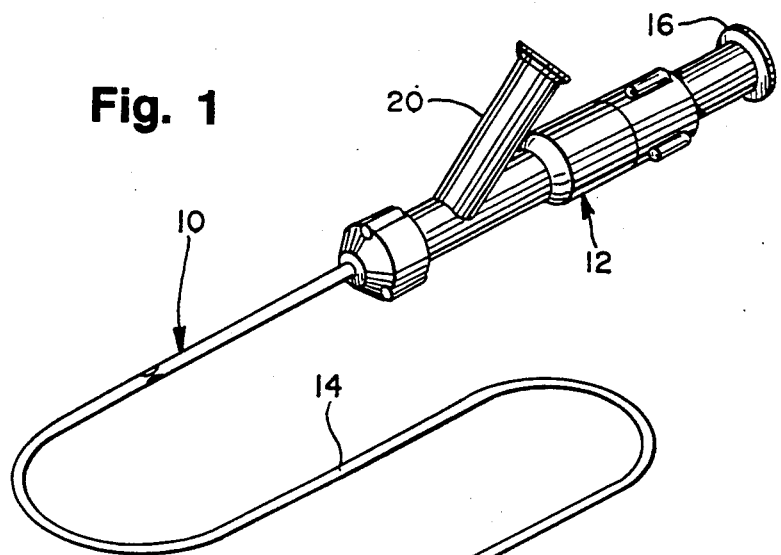
Fig. 1
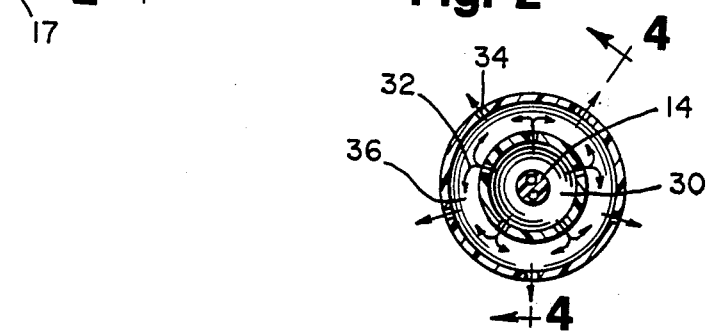
Fig. 2
Fig. 3
Fig. 4

THERAPEUTIC POROUS BALLOON CATHETER

BACKGROUND OF THE INVENTION

In the prior art, for example Shockey et al. U.S. Pat. No. 4,994,033 and the C. R. Bard, Inc. European patent application no. 383,429 A2, published Aug. 22, 1990, a catheter is taught for the application of medication to a blood vessel wall, for example to a stenosis. The medication is administered through a balloon in the catheter which carries an array of minute holes or micropores, so that the medication may flow into the balloon through a lumen in the catheter, and then by the action of pressurization in the balloon it is forced out of the holes or micropores.

It has been found that at pressures of about two atmospheres and above, the velocity of fluid that passes out of the holes of such a balloon often can create a forceful stream which directly impinges the arterial wall. This, in turn, can actually cause tissue damage, even to the extent of extending and increasing the dissection within the arterial wall which is caused by an angioplasty procedure such as PTCA.

Thus, there is a need for a therapeutic balloon catheter for administering medication to the artery wall in which the medication can be administered under a reasonable pressure for rapid flow of medication out of a perforated balloon, but the forceful stream is avoided, so that the fluid does not forcefully impinge the arterial wall, but rather "weeps" out of the perforations in a substantial but non-damaging manner.

DESCRIPTION OF THE INVENTION

In accordance with this invention a balloon catheter is provided which comprises a catheter shaft, having first and second balloons carried on the catheter shaft, with the second balloon being positioned to at least partially overlie and sealingly enclose the first balloon. At least one lumen is defined by the catheter shaft, which lumen communicates between a space located within the first balloon and outside of the catheter shaft, so that medication occupying such space will be captured between the first balloon and the catheter shaft.

Both the first and second balloons used in this invention define holes (which may be slits) which are of a size to permit medication delivered through the lumen to pass outwardly through the holes of both of the first and second balloons. Thus, the various pressurized streams of medication which come through the first, inner balloon tend to impinge the second, outer balloon and not the tissue of the artery or other portion of the body in which the catheter resides. The effect of this is to reduce or eliminate the tissue injury that can take place by this mode of medication administration.

Preferably, the holes of the first balloon are displaced out of registry with the holes of the second balloon, to increase the protective effect that the outer, second balloon may have on the tissue in which the catheter is emplaced, as pressurized medication liquid is administered. Specifically, the holes of the first balloon may be circumferentially spaced from the holes of the second balloon, or longitudinally spaced from the holes of the second balloon, or both.

The first and second balloons may be tubular, with, preferably, one end of each of the first and second balloons defining a common, annular seal with the catheter shaft. It is also preferable for the first balloon to be shorter than the second balloon, with the ends of the balloons which are opposed to the one end described above each defining a separate, annular seal with the catheter shaft.

It is also preferable for the catheter of this invention to be of the over-the-wire type, defining a second lumen for such a guidewire, in a manner which is generally conventional except as otherwise described herein.

As a modification of this invention, a tubular, porous, liquid-permeable member may be positioned between the first and second balloons to provide further protection to the outer tissues against impinging streams of medication. For example, such a tubular, porous, liquid permeable member may comprise a plastic material of open cell foam or expanded, fibrous plastic. Such open cell foams are well-known, as are expanded, fibrous plastics. For example, polytetrafluoroethylene expanded, fibrous plastic sheeting is sold by W.L. Gore Inc. of Flagstaff, Ariz. under the trademark GORE-TEX. Also, cellulose or polyethylene paper may be used. The tubular, porous, liquid permeable material may also be a porous sheet or membrane, typically having holes of a diameter of about 0.2 to 30 microns. Specifically, a polycarbonate membrane may be used such as Poretics polycarbonate Track-Etch (PCTE T.M.) membrane filters.

As a further modification, a tubular, porous, liquid permeable member as described above may be bonded to one of the first or second balloons in a position to extend across the perforations thereof, for further protection against streaming liquid damage of tissues outside of the catheter.

As a further alternative, at least one of the balloons themselves, for example the outer, second balloon, may comprise such an open-cell foam or expanded, fibrous plastic, or porous membrane, being capable of permeation by liquids at the administration pressures contemplated.

Typically, the second balloon expands to a diameter that is about 10 to 30 percent larger than the diameter of the first balloon. The holes of the respective balloons are typically about 15 to 30 microns in diameter and are present in a relatively large number across the face of about the central two-thirds of the balloons, being typically spaced from the ends thereof. As is typical for angioplasty, the balloons are preferably made of flexible but relatively non-elastomeric material.

Thus, tissues are protected by the double balloon therapeutic catheter of this invention, while large amounts of well-distributed medication are applied exactly to the desired local area, typically within a blood vessel such as an artery, but broadly wherever the catheter may be emplaced in the body.

DESCRIPTION OF DRAWINGS

In the drawings, FIG. 1 is a perspective view of the catheter of this invention;

FIG. 2 is a cross-sectional view taken along line 2—2 of FIG. 1;

FIG. 3 is a cross-sectional view taken along line 3—3 of FIG. 1;

FIG. 4 is a sectional view taken along line 4—4 of FIG. 2;

DESCRIPTION OF SPECIFIC EMBODIMENTS

Figure 5:
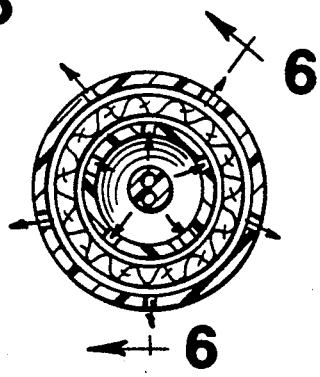
FIG. 5 is a transverse sectional view of another embodiment of the catheter of this invention, generally analogous to FIG. 2.

Referring to FIGS. 1 through 3, catheter 10 may be a conventional over-the-wire catheter, modified in accordance with this invention. Catheter 10 defines a conventional hub 12 and a catheter body 14, which defines a pair of lumens 17, 19. Lumen 17 connects to the guide wire hub port 16 for receiving a guidewire. The other lumen 19 communicates with medication supply port 20 of hub 12, so that lumen 19 may convey medication to the distal end of the catheter.

Guidewire lumen 17 typically extends through the entire length of the catheter, exiting at its distal end 22. Lumen 19, on the other hand, typically terminates in one or more side openings 24 (FIG. 3) which are positioned short of the distal end within a pair of overlapping, sealed tubular balloons 26, 28.

Thus, catheter 10 can be advanced along a guidewire with the guidewire occupying lumen 17, until the catheter occupies a position with its distal end typically in the arterial system of a patient. Then, medication can be administered through port 20 and lumen 19, to flow into space 30 defined between catheter shaft 14 and inner balloon 26.

The respective balloons 26, 28 may be made of any desired plastic material, particularly plastic materials which are conventionally used for arterial catheter balloons such as nylon or poly(ethylene terephthalate). As shown, both inner balloon 26 and outer balloon 28 respectively define a plurality of holes 32, 34. Such holes are sized to permit the medication administered into space 30 to pass outwardly through both balloons at the intended pressures to be applied to the medication within lumen 19. Specifically, the holes 32, 34 may be about 25 microns in diameter, the holes being placed circumferentially about each cylindrical balloon in approximately the central two-thirds of each balloon.

Thus, as the respective balloons are expanded by the pressure of medication therein, the outer balloon 28 typically places its holes 34 directly against the tissue within which the catheter balloons reside, such as arterial wall tissue. The medication is directly conveyed from the outer holes 34 into the arterial wall tissue.

Preferably, a large number of holes 32, 34 are provided in the balloon, for example with a spacing of about one hole per square millimeter of balloon surface within the central portion thereof, so that an abundant supply of medication can be directly applied to the tissues surrounding the catheter balloon.

Pressurized medication liquid from space 30 is forcefully expelled through holes 32 of inner balloon 26, with a relatively forceful stream of medication coming out of each of holes 32. However, it can be seen that the medication stream from each of holes 32 directly impinges an inner wall of outer balloon 28 rather than directly striking tissue in which the catheter is emplaced. Then, the medication liquid migrates about in turbulent manner in space 30, eventually passing out of holes 34 in outer balloon 28, but in a stream that is substantially less forceful than the stream of fluid passing out of perforations 32 because of the turbulence and reduced pressure found within space 36, when compared with space 30.

Accordingly, damage of tissue positioned immediately outside of balloon 28 is significantly reduced and even eliminated.

The catheter of this invention may be used to deliver therapeutic agents to a site in the arterial wall after angioplasty, or it may be used to deliver various therapeutic substances to other arterial or venous wall sites, or other tissue sites. Examples of medications which might be delivered include antithrombolytic agents such as heparin, anti-spasmodic agents, chemotherapeutic agents, agents for embolic therapy, or any other desired medication, specifically those that require specific site or local applications. For example, a chemotherapeutic agent could be delivered directly to a tumor site in the bladder, liver, kidney or the like. Also, the invention of this application may be used in conjunction with a fixed-wire type catheter or an other desired type of catheter.

It can be seen from both FIGS. 2 and 4 that the perforations 32 are both circumferentially and longitudinally spaced from the perforations 34 of second balloon 28. The longitudinal spacing of the respective perforations is shown in FIG. 4, while the circumferential spacing is shown in FIG. 2. This assures that the streams of fluid forcefully passing out of holes 32 of inner balloon 26 impinge on a wall of second balloon 28 rather than passing directly through a hole 34 into direct impinging contact with the tissue outside of balloon 28.

First and second balloons 26, 28 may be sealed together and to catheter shaft 14 in a common, annular seal 31, which may be a radio frequency heat seal or any other desired seal. At the other end of the respective balloons 26, 28, annular seals 33, 35 of similar nature may be provided between the ends of the balloons and catheter shaft 14, since inner balloon 26 is typically shorter than outer balloon 28.

Figure 6:
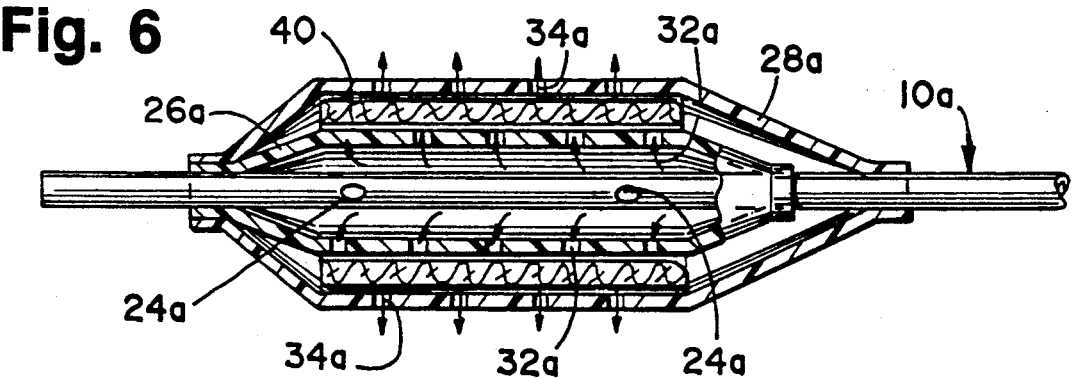
FIG. 6 is a longitudinal sectional view taken along line 6—6 of FIG. 5.

Referring to FIGS. 5 and 6, the distal balloon portion of catheter 10a is disclosed, being similar in construction to the catheter of FIGS. 1-3 except as otherwise described herein.

As before, balloons 26a, 28a are affixed to catheter shaft 10a in sealing manner similar to the previous embodiment. Appropriate holes 24a are defined in catheter shaft 10a communicating with a medication supply lumen, while another lumen is present for a guidewire in catheter shaft 10a if desired.

Each of balloons 26a, 28a defines holes 32a, 34a as in the previous embodiment for similar purposes.

However, in this embodiment, a tubular sheath 40 of porous, liquid permeable material is provided between the respective balloons 26a, 28a so that the forceful flow from holes 32a strikes the porous member 40, to further provide protection against a direct stream of fluid striking tissue. In this embodiment, even if respective holes 32a, 34a are aligned, the presence of porous, liquid permeable member 40 can break up the streaming flow out of perforations 32a so that a gentle flow of medication passes out of outer apertures 34a.

The porous, tubular, liquid permeable member 40 may, as stated before, be made of an open cell foam material, an expanded, fibrous plastic, or a porous membrane, which materials are well-known. Expanded, fibrous plastics comprise micro-fibrous, flexible materials which generally have a structure resembling fibers joined together at intersection points. For example, expanded polytetrafluoroethylene is a well-known material of this type.

Thus, medication can be administered with the catheter of the design of FIGS. 5 and 6 with greatly reduced or eliminated tissue damage.

Figure 7:
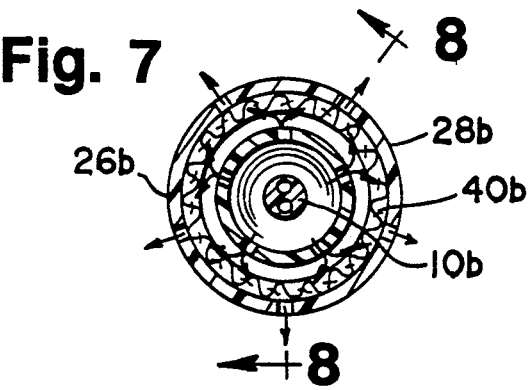
FIG. 7 is a transverse sectional view of a third embodiment of the invention, generally analogous to FIG. 2.
Figure 8:
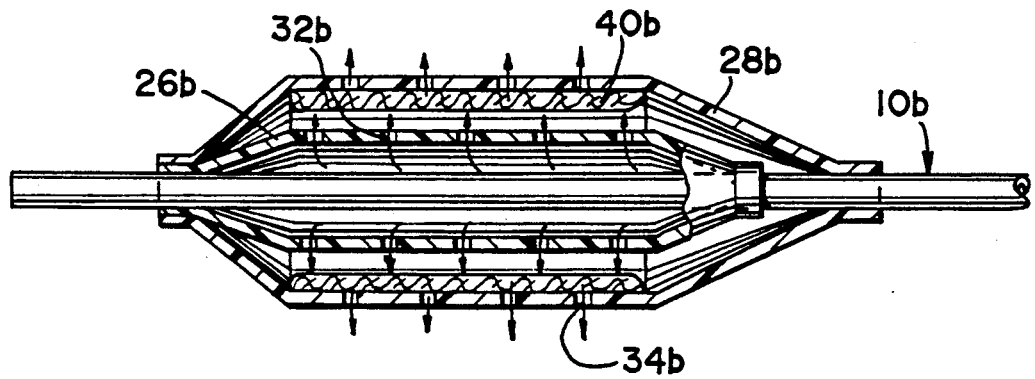
FIG. 8 is a longitudinal sectional view taken along line 8—8 of FIG. 7.

Turning to FIGS. 7 and 8, another embodiment is disclosed. Catheter 10b, as before, carries a pair of sealed, overlying balloons 26b, 28b having holes or apertures 32b, 34b in a manner similar to the previous embodiments.

However, in this embodiment, tubular, porous liquid permeable member 40b is bonded to the inner surface of outer balloon 28a to assure its adherence in position.

Alternatively, the entire outer balloon 28b may be made of a porous, liquid permeable material such as an open cell foam, an expanded fibrous plastic sheet, or a microporous membrane such as polycarbonate, so that an extra tubular length of material is not necessary, but the streams of liquid from inner holes 32b may still be prevented from directly striking tissue outside of balloon 28b. Such a structure would actually resemble the structure of FIGS. 2 and 4, with outer balloon 28 being made of such material. Alternatively, inner balloon 26 or 26b could be made of such an open cell foam, or an expanded, fibrous plastic, or a microporous membrane.

Alternatively, any of holes 32, 34 in any embodiment may be replaced by slits, particularly slits having sides that close together in the absence of a pressure differential thereacross. Such slits are intended to be included in the term "holes".

One advantage of using such slits, or a foam or expanded, fibrous plastic made of a hydrophobic material, is that the medication will not substantially bleed out of the balloons until a given minimum pressure is applied thereto, to force the fluid out. Thus, the catheter can be advanced with the lumen and balloon containing medication, without any major loss of medication from within the balloon system until the catheter has been desirably emplaced.

The above has been offered for illustrative purposes only and is not intended to limit the scope of the invention of this application, which is as defined in the claims below.

That which is claimed is:

1. A balloon catheter which comprises a catheter shaft, first and second balloons carried on said catheter shaft with said second balloon positioned to at least partly overlie and sealingly enclose said first balloon; a lumen defined by said catheter shaft which communicates between a space located within said first balloon and a proximal end portion of said catheter shaft; said first and second balloons defining holes of a size to permit medication delivered through said lumen to pass outwardly through the perforations of both the first and second balloons.

2. The catheter of claim 1 in which said second balloon completely encloses said first balloon.

3. The catheter of claim 2 in which said first and second balloons are tubular, one end of each of said first and second balloons defining a common, annular seal with said catheter shaft.

4. The catheter of claim 3 in which said first balloon is shorter than said second balloon, the ends of said balloons opposed to said one end each defining a separate, annular seal with said catheter shaft.

5. The catheter of claim 1 in which the holes of the first balloon are displaced out of registry with the holes of the second balloon.

6. The catheter of claim 5 in which the holes of the first balloon are circumferentially spaced from the holes of the second balloon.

7. The catheter of claim 6 in which the holes of the first balloon are longitudinally spaced from the perforations of the second balloon.

8. The catheter of claim 5 in which the perforations of the first balloon are longitudinally spaced from the perforations of the second balloon.

9. The catheter of claim 1 in which said catheter shaft defines a second lumen for receiving a guidewire.

10. The catheter of claim in which a tubular, porous, liquid-permeable member is positioned between said first and second balloons.

11. The catheter of claim 10 in which said tubular, porous member is selected from the group consisting of open-cell foam, expanded, fibrous plastic, and a porous membrane.

12. The catheter of claim 1 in which at least one of said balloons comprises open-cell foam or expanded, fibrous plastic.

13. The catheter of claim in which a tubular, porous, liquid permeable member is bonded to one of said first and second balloons in a position to extend across the perforations thereof.

14. The catheter of claim 13 in which said tubular, porous member comprises open-cell foam or expanded, fibrous plastic.

15. The catheter of claim 1 in which said second balloon expands to a diameter that is about 10 to 30 percent larger than the diameter of said first balloon.

16. The catheter of claim 1 in which the holes of said balloons are about 15 to 30 microns in diameter.

17. A balloon catheter which comprises a catheter shaft, first and second balloons carried on said catheter shaft with said second balloon positioned to sealingly enclose the first balloon; a lumen defined by said catheter shaft which communicates between a space located within said first balloon and a proximal end portion of said catheter shaft; said first and second balloons defining holes of a size to permit medication delivered through said lumen to pass outwardly through the holes of both the first and second balloons; the holes of the first balloon being displaced out of registry with the holes of the second balloon.

18. The catheter of claim 17 in which the holes of the first balloon are circumferentially spaced from the holes of the second balloon.

19. The catheter of claim 18 in which the holes of the first balloon are longitudinally spaced from the holes of the second balloon.

20. The catheter of claim 17 in which said first and second balloons are tubular, one end of each of said first and second balloons defining a common annular seal with said catheter shaft, said first balloon being shorter than said second balloon, the ends of said balloons opposed to said one end each defining a separate, annular seal with said catheter shaft.

21. The catheter of claim 17 which defines a second lumen for receiving a guidewire.

22. A balloon catheter which comprises a catheter shaft, first and second balloons carried on said catheter shaft with said second balloon positioned to sealingly enclose said first balloon; a lumen defined by said catheter shaft which communicates between a space located within said first balloon and a proximal end portion of said catheter shaft; said first and second balloons defining holes of a size to permit medication delivered through said lumen to pass outwardly through the holes of both the first and second balloons, said first and second balloons and the space therebetween comprising at least one tubular, porous, liquid-permeable member made of open-cell foam or expanded, fibrous plastic.

23. The catheter of claim 22 in which at least one of said balloons comprises said open-cell foam or expanded, fibrous plastic tube.

24. The catheter of claim 22 in which said tubular, open-cell foam or expanded, fibrous plastic is carried between said first and second balloons.

25. The catheter of claim 22 in which said tubular, open-cell foam or expanded, fibrous plastic is bonded to one of said balloons.

26. A balloon catheter which comprises a catheter shaft and a balloon carried on said catheter shaft, a lumen defined by said catheter shaft which communicates between a space located within said balloon and a proximal end portion of said catheter shaft, said balloon comprising a plurality of holes of a size to permit medication delivered through said lumen to pass outwardly through said holes, said balloon carrying a tubular, microporous membrane covering said holes to break up streams of flowing medication the microporous membrane having pores that are smaller than the balloon holes.

27. The catheter of claim 26 in which said balloon defines a central, cylindrical portion and tapered end portions having minimum diameter ends adhered to the catheter shaft, said tubular microporous membrane being carried by the cylindrical portion of said balloon and spaced from the tapered end portions.

28. The catheter of claim 27 in which said tubular microporous membrane is made of polycarbonate resin.

* * * * *